United States Patent
Colby et al.

(10) Patent No.: US 11,587,646 B2
(45) Date of Patent: Feb. 21, 2023

(54) METHOD FOR SIMULTANEOUS CHARACTERIZATION AND EXPANSION OF REFERENCE LIBRARIES FOR SMALL MOLECULE IDENTIFICATION

(71) Applicant: Battelle Memorial Institute, Richland, WA (US)

(72) Inventors: Sean M. Colby, Richland, WA (US); Ryan S. Renslow, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 709 days.

(21) Appl. No.: 16/702,119

(22) Filed: Dec. 3, 2019

(65) Prior Publication Data
US 2020/0176087 A1 Jun. 4, 2020

Related U.S. Application Data

(60) Provisional application No. 62/774,663, filed on Dec. 3, 2018.

(51) Int. Cl.
*G16C 20/20* (2019.01)
*G16C 20/30* (2019.01)
(Continued)

(52) U.S. Cl.
CPC ............. *G16C 20/20* (2019.02); *G06N 3/08* (2013.01); *G06N 20/10* (2019.01); *G16C 20/30* (2019.02);
(Continued)

(58) Field of Classification Search
None
See application file for complete search history.

(56) References Cited

U.S. PATENT DOCUMENTS 10,885,111 B2 * 1/2021 Chaudhury ............. G06F 16/86
2016/0378912 A1 * 12/2016 Ragno ..................... G16C 20/60
506/8

OTHER PUBLICATIONS

Alperstein et al., All SIMLES Variational Autoencoder, 2019, Arxiv, https://doi.org/10.48550/arXiv.1905.13343 (Year: 2019).*

(Continued)

*Primary Examiner* — Roy Y Yi
(74) *Attorney, Agent, or Firm* — Haverstock & Owens, A Law Corporation

(57) ABSTRACT

A variational autoencoder (VAE) has been developed to learn a continuous numerical, or latent, representation of molecular structure to expand reference libraries for small molecule identification. The VAE has been extended to include a chemical property decoder, trained as a multitask network, to shape the latent representation such that it assembles according to desired chemical properties. The approach is unique in its application to metabolomics and small molecule identification, focused on properties that are obtained from experimental measurements (m/z, CCS) paired with its training paradigm, which involves a cascade of transfer learning iterations. First, molecular representation is learned from a large dataset of structures with m/z labels. Next, in silico property values are used to continue training. Finally, the network is further refined by being trained with the experimental data. The trained network is used to predict chemical properties directly from structure and generate candidate structures with desired chemical properties. The network is extensible to other training data and molecular representations, and for use with other analytical platforms, for both chemical property and feature prediction as well as molecular structure generation.

33 Claims, 7 Drawing Sheets

(51) Int. Cl.
*G16C 60/00* (2019.01)
*G06N 20/10* (2019.01)
*G16C 20/60* (2019.01)
*G06N 3/08* (2006.01)
*G16C 20/70* (2019.01)

(52) U.S. Cl.
CPC ............ *G16C 20/60* (2019.02); *G16C 20/70* (2019.02); *G16C 60/00* (2019.02)

(56) References Cited

OTHER PUBLICATIONS

Cid, Bioactivity-oriented de novo design of small molecules by conditional variational autoencoders, 2019, Universitat de Barcelona, p. 1-42 (Year: 2019).*

* cited by examiner

METHOD FOR SIMULTANEOUS CHARACTERIZATION AND EXPANSION OF REFERENCE LIBRARIES FOR SMALL MOLECULE IDENTIFICATION

CROSS-REFERENCE TO RELATED APPLICATION(S)

This application claims priority under 35 U.S.C. § 119(e) of the U.S. Provisional Patent Application Ser. No. 62/774,663, filed Dec. 3, 2018 and titled, "METHOD FOR SIMULTANEOUS CHARACTERIZATION AND EXPANSION OF REFERENCE LIBRARIES FOR SMALL MOLECULE IDENTIFICATION," which is hereby incorporated by reference in its entirety for all purposes.

STATEMENT AS TO RIGHTS TO DISCLOSURES MADE UNDER FEDERALLY-SPONSORED RESEARCH AND DEVELOPMENT

The invention was made with government support under Contract DE-AC0576RL01830 awarded by the U.S. Department of Energy. The Government has certain rights in the invention.

FIELD OF THE INVENTION

The present invention relates to molecule identification, chemical property prediction, and small molecule structure generation. More specifically, the present invention relates to a new deep learning architecture, training modality, and training set for the use of characterization of molecules in samples, drug design and other small molecule generation modes, and chemical property prediction broadly.

BACKGROUND OF THE INVENTION

Robust and comprehensive identification of small metabolites in complex samples could revolutionize the understanding of metabolic interactions in biological systems. Existing and emerging technologies have enabled measurement of chemical properties of molecules in complex mixtures and, in concert, are sensitive enough to resolve even stereoisomers. Despite these experimental advances, small molecule identification is typically inhibited by (i) a deficiency in reference properties (e.g. mass spectra, collisional cross section, and other measurable properties), limiting the number of possible identifications, and (ii) the lack of a method to generate candidate matches from experimental features. Furthermore, small molecule design and structure generation needs to be informed by desired chemical properties. A method that can both predict properties for use in identifying chemical mixtures and also generate molecular structures would advance many scientific fields and industry goals.

SUMMARY OF THE INVENTION

A Variational AutoEncoder (VAE) has been developed to learn a continuous numerical, or latent, representation of molecular structure, to simultaneously characterize and expand reference libraries for small molecule identification. The VAE has been extended to include a chemical property decoder, trained as a multitask network, in order to shape the latent representation such that it assembles according to desired chemical properties. The approach is unique in its application to metabolomics and small molecule identification, its focus on properties that can be obtained from experimental instruments (e.g., mass, collision cross section (CCS)), and its training paradigm, which involves a cascade of transfer learning iterations. First, molecular representation is learned from a large dataset of unlabeled structures. Next, properties calculated in silico are used to continue training with property prediction, as experimental property data is limited. Finally, the network is trained with the limited experimental data. This allows the network to learn as much as possible at each stage, enabling success with progressively smaller datasets without overfitting.

Once trained, the network is able to be used to predict chemical properties directly from structure, as well as generate candidate structures with chemical properties similar to some arbitrary input. The approach described herein is orders of magnitude faster than first-principles simulation for property prediction. Additionally, the ability to generate molecules along manifolds defined by chemical property analogues positions the system/framework (e.g., DarkChem) as highly useful in a number of application areas, including metabolomics and small molecule identification, drug discovery and design, chemical forensics, and beyond.

In one aspect, a method of simultaneous characterization and expansion of reference libraries for small molecule identification comprises extending a variational autoencoder (VAE) to include a chemical property decoder, so as to form an extended VAE, training the extended VAE as a multi-task network, to shape a latent representation that self-assembles according to preselected criteria, and finding correlations embedded in the latent representation, wherein the correlations embedded in the latent representation enable prediction of chemical properties from structures generated along manifolds defined by chemical property analogues. Training includes processing a cascade of transfer learning iterations comprising: a first dataset of unlabeled structures, a second dataset of properties calculated in silico and a third dataset of limited experimental data for fine tuning. The first dataset is larger than the second dataset, and the second dataset is larger than the third dataset. An output of processing the cascade of transfer learning iterations comprises a set of weights. The correlations embedded in the latent representation enable prediction of the structures from the chemical properties. The method further comprises implementing character embedding to learn relationships among different characters or symbols that are used to represent molecular structure (e.g., as in SMILES or InChI molecular structure representations). The method further comprises implementing a beam search to enable the vector representation of a structure to be converted back into multiple, most-probable full structures. This allows a user to sample the latent representation for new molecules that have not been found before. The method further comprises implementing a global attention mechanism which informs a user why certain chemical bonds are giving certain properties. The method further comprises implementing a molecular structure discriminator which is an added deep learning network that determines whether a structure is both syntactically and chemically valid. The method further comprises implementing a molecular structure discriminator which is used to modify a training loss function during training of the VAE, such that the latent space would be penalized for and therefore be trained to avoid creating structures that have physically/chemically invalid bonding types, molecular topologies, and/or nonbonding interactions. The method further comprises implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

The method further comprises implementing encoding (e.g. mapping) of chemical and enzymatic reactions in the latent space such that novel molecules can be found by starting with known molecules and following mapped reactions to discover new molecules. These new molecules may represent real previously-unknown molecules that can be biologically- or chemically-derived through known reactions. Briefly, known chemical reactions (e.g., known biotic and abiotic reactions; metabolic pathway ontologies from online databases such as MetaCyc) would be mapped onto latent space, and new molecules would be generated following these patterns into new latent space locations. The appeal to this approach is that chemical reaction "math" within latent space could be possible by defining reaction vectors. As a possible example, theobromine minus caffeine (representing the demethylation reaction) plus ethyltheophylline (T-C+E) could result in the latent space location of demethylated ethyltheophylline (i.e., 7-ethyl-3-methyl-3,7-dihydro-1H-purine-2,6-dione). In this manner, new molecules that are chemically possible through known reactions could reduce the massive search space and result in high probability structures that result from existing biological, biogeochemical, and industrial processes. To be more specific, a mapped chemical reaction product vector is found by adding (or other arithmetic or mathematical transformations) the reaction vector to a reactant vector. The product vector provides the location of the product molecule in latent space, which can subsequently be decoded into a structure representation. Generally speaking, a reaction vector may be calculated by taking a product vector and subtracting its reactant vector. However, the reaction vector used to predict chemical products may be the average of a list of reaction vectors under the condition of the same reaction type. For example, suppose there are 10 chemical reduction reactions, from carbon-carbon double bond to single bond. Each reaction vector is computed first, and then the 10 calculated vectors are averaged as the prediction reaction vector. The reason why average reaction vectors may be selected is obvious, as an average reaction vector enables achieving better product predictions compared to a random single reaction vector with the premise of an equal reaction type. This process of averaging and performing mathematical operations on known reaction-product pairs and their latent space vectors is used to map the reactions onto latent space. In some cases, searching around the latent space volume dictated by a mapped reaction may result in similar novel molecule compounds and can be used to fill chemical space with related molecules, including those that may arise from chemical side reactions.

In another aspect, an apparatus comprises a memory configured for storing an application, the application configured for: extending a variational autoencoder (VAE) to include a chemical property decoder, so as to form an extended VAE, training the extended VAE as a multi-task network, to shape a latent representation that self-assembles according to preselected criteria, and finding correlations embedded in the latent representation, wherein the correlations embedded in the latent representation enable prediction of chemical properties from structures generated along manifolds defined by chemical property analogues and a processor configured for processing the application. Training includes processing a cascade of transfer learning iterations comprising: a first dataset of unlabeled structures, a second dataset of properties calculated in silico and a third dataset of limited experimental data for fine tuning. The first dataset is larger than the second dataset, and the second dataset is larger than the third dataset. An output of processing the cascade of transfer learning iterations comprises a set of weights. The correlations embedded in the latent representation enable prediction of the structures from the chemical properties. The application is further configured for implementing character embedding to learn relationships among different characters or symbols that are used to represent molecular structure (e.g., as in SMILES or InChI molecular structure representations). The application is further configured for implementing a beam search to enable the vector representation of a structure to be converted back into multiple, most-probable full structures. This allows a user to sample the latent representation for new molecules that have not been found before. The application is further configured for implementing a global attention mechanism which informs a user why certain chemical bonds are giving certain properties. The application is further configured for implementing a molecular structure discriminator which is an added deep learning network that determines whether a structure is both syntactically and chemically valid. The application is further configured for implementing a molecular structure discriminator which is used to modify a training loss function during training of the VAE, such that the latent space would be penalized for and therefore be trained to avoid creating structures that have physically/chemically invalid bonding types, molecular topologies, and/or non-bonding interactions. The application is further configured for implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

In another aspect, a system comprises a first device for storing training data and a second device configured for: extending a variational autoencoder (VAE) to include a chemical property decoder, so as to form an extended VAE, training the extended VAE as a multi-task network using the training data, to shape a latent representation that self-assembles according to preselected criteria, and finding correlations embedded in the latent representation, wherein the correlations embedded in the latent representation enable prediction of chemical properties from structures generated along manifolds defined by chemical property analogues and a processor configured for processing the application. Training includes processing a cascade of transfer learning iterations comprising: a first dataset of unlabeled structures, a second dataset of properties calculated in silico and a third dataset of limited experimental data for fine tuning. The first dataset is larger than the second dataset, and the second dataset is larger than the third dataset. An output of processing the cascade of transfer learning iterations comprises a set of weights. The correlations embedded in the latent representation enable prediction of the structures from the chemical properties. The second device is further configured for implementing character embedding to learn relationships among different characters or symbols that are used to represent molecular structure (e.g., as in SMILES or InChl molecular structure representations). The second device is further configured for implementing a beam search to enable the vector representation of a structure to be converted back into multiple, most-probable full structures. This allows a user to sample the latent representation for new molecules that have not been found before. The second device is further configured for implementing a global attention mechanism which informs a user why certain chemical bonds are giving certain properties. The second device is further configured for implementing a molecular structure discriminator which is an added deep learning network that determines whether a structure is both syntactically and chemically valid. The second device is further configured for implementing a molecular structure discriminator which is used to modify a training loss function during training of the VAE, such that the latent space would be penalized for and therefore be trained to avoid creating structures that have physically/chemically invalid bonding types, molecular topologies, and/or nonbonding interactions. The second device is further configured for implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

BRIEF DESCRIPTION OF AN EMBODIMENT

Figure 1:
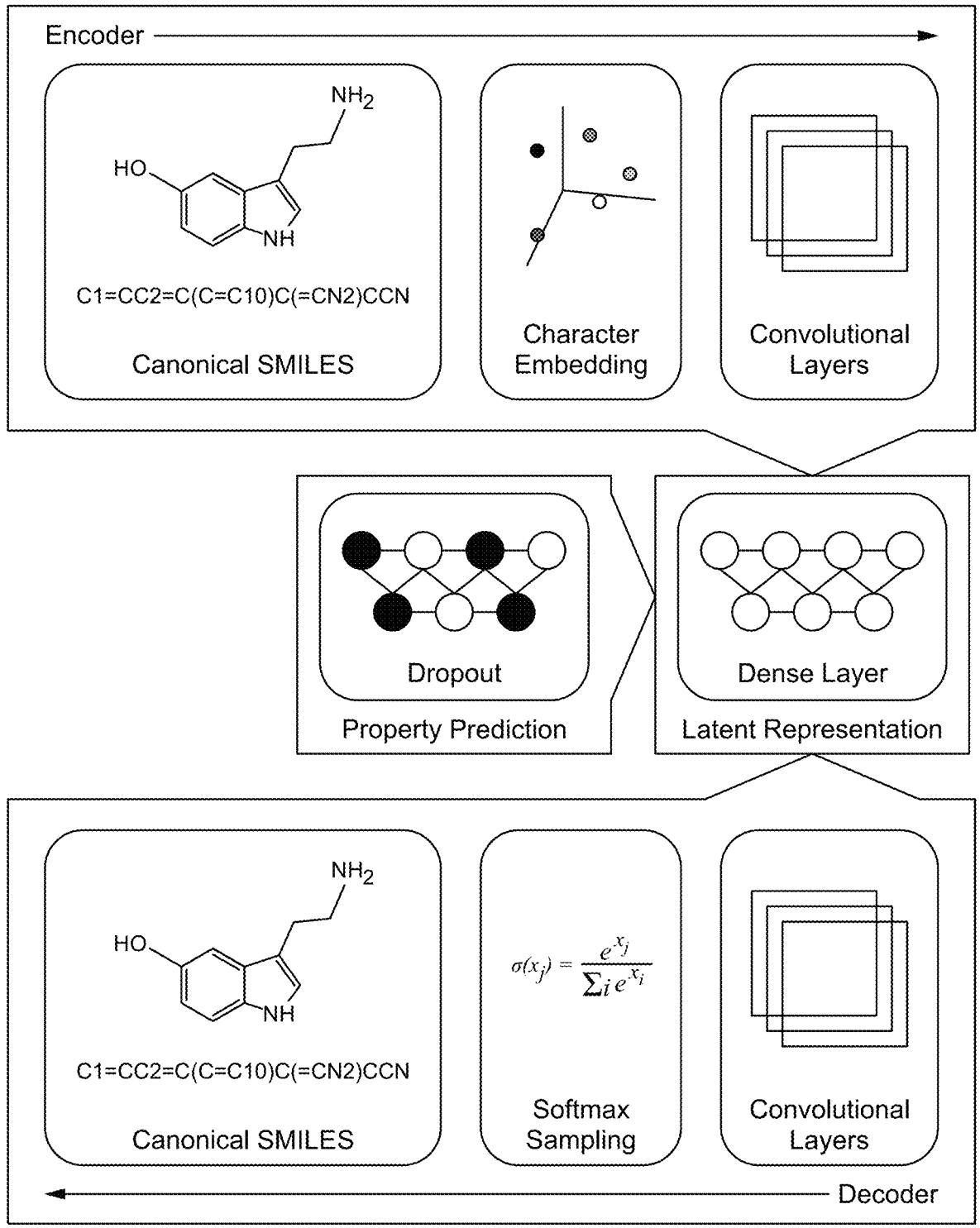
FIG. 1 illustrates a network schematic according to some embodiments.

In some embodiments, the method is implemented as a framework (e.g., DarkChem). DarkChem is a deep learning framework designed to simultaneously characterize and expand reference libraries for small molecule identification, e.g. metabolomics or exposomics. Through training, DarkChem learns an encoding of molecular structure and chemical properties of interest, which can then be perturbed to yield additional, potentially novel candidates with similar structure, properties, or both. This configuration enables novel molecule discovery from previously unidentifiable metabolomics features in complex biological mixtures.

Existing and emerging technologies have enabled measurement of chemical properties of molecules in complex mixtures and, in concert, are sensitive enough to resolve even stereoisomers. Despite these experimental advances, small molecule identification is inhibited by (i) a deficiency in reference properties (e.g. mass spectra, collisional cross section, and other measurable properties), limiting the number of possible identifications, and (ii) the lack of a method to generate candidate matches from experimental features. DarkChem is powered by a variational autoencoder (VAE). It is able to learn a continuous numerical, or latent, representation of molecular structure to simultaneously characterize and expand reference libraries for small molecule identification.

The VAE is extended to include a chemical property decoder, trained as a multi-task network, in order to shape the latent representation such that it self-assembles according to said properties, e.g., collision cross section. Correlations are found embedded in the latent representation, enabling molecule generation along manifolds defined by chemical property analogues. Thus, the network can be used to predict chemical properties from structure, as well as generate candidate structures with desired chemical properties. While similar approaches exist in the literature, DarkChem is unique in its application to metabolomics and small molecule identification, its focus on properties that can be obtained from experimental instruments (mass, CCS, formula), and its unique training paradigm. DarkChem is trained by a cascade of transfer learning iterations: first, molecular representation is learned from a large dataset of unlabeled structures. Next, properties calculated in silico (e.g., through first-principles simulation, e.g., via the In Silico Chemical Library Engine, ISiCLE, a molecular dynamics and quantum chemistry-based work flow used to automate chemical property predictions) are used to continue training with property prediction, as experimental property data is limited. Finally, the network is trained with the limited experimental data for fine tuning. This allows DarkChem to learn as much as possible at each stage, enabling success with progressively smaller datasets without overfitting. DarkChem is orders of magnitude faster than first-principles simulation for property prediction. Additionally, the ability to generate molecules along manifolds defined by chemical property analogues positions DarkChem as highly useful in a number of application areas, including metabolomics and small molecule identification, drug discovery and design, chemical forensics, and beyond.

High throughput small molecule identification in complex samples typically utilizes the comparison of experimental features (e.g., m/z, chromatographic retention times) to corresponding reference values in libraries in order to build evidence for the presence of a particular molecule. Libraries can be determined experimentally through analysis of authentic reference materials (e.g., standards), or through in silico calculation of chemical properties and prediction of analytical features. The former is preferred, and is currently the gold standard approach for library-building, primarily due to the assumed lower associated variance for properties derived from modern analytical platforms, and thus higher levels of assigned confidence to identifications. However, most compounds are not available for purchase as authentic reference material, cannot be isolated or easily synthesized, or are simply yet unknown. In addition, the experimental route for library building is costly and time consuming. In contrast, in silico methods can yield reference values rapidly, facilitating the creation of much larger libraries than reasonably achievable through experimental methods.

In silico library-building methods for applications in metabolomics vary, ranging from first-principles physics simulations, to property-based machine learning approaches. While useful, both methods have limitations: first-principles approaches can require a deep understanding of the underlying physics, which may not be well understood, and substantial compute time to yield accurate predictions. Furthermore, it is currently infeasible to use first-principles-based methods in a generative manner, e.g., to directly create molecular structures with desired properties. Conversely, machine learning approaches generally utilize large training sets and predictions are typically constrained to molecules similar to those found within the training set. Thus, machine learning approaches may not necessarily generalize to novel molecules outside of the chemical classes represented by the training set.

Recent interest in chemical structure-based deep learning solutions have shown promise, ranging from graph convolutional and recurrent neural networks; generative approaches, including autoencoder and adversarial networks; reinforcement learning approaches; as well as hybrid implementations. Of particular interest are those generative approaches that learn a continuous numerical, or latent, representation of molecular structure. These networks take SMILES (simplified molecular line entry system) strings, molecular graphs, or other molecular structure representations as input and, in a semi-supervised configuration, predict the same structural representation as output. Importantly, recent works have begun coupling the latent representation of molecular structure to property predictor subnetworks. This yields latent space entanglement, wherein the vectors describing molecular inputs begin to encode both structure and property, with implications in inverse quantitative structure-activity/property relationship (QSAR, QSPR) through "molecular optimization." That is, traversing the latent space to generate molecules with desired properties. However, these deep learning applications have been limited to materials design and/or discovery, which has been reflected in the properties predicted, as well as the datasets on which these networks have been trained.

Here, a deep learning approach is described, referred to as DarkChem, that builds upon previous variational autoencoder (VAE) work and focuses on predicting chemical properties for use in metabolomics and non-targeted small molecule identification. DarkChem is demonstrated for (i) property prediction to create a massive in silico library, (ii) an initial small molecule identification test application, and (iii) example novel molecule generation, all focused on m/z (obtained from mass spectrometry after ionization) and collision cross section (CCS; obtained from ion mobility spectrometry). These properties have been demonstrated, in concert, to build evidence for the presence of molecules in complex biological samples. The mass-to-charge ratio has a long history for use in compound identification, and is a core feature around which most identifications are anchored in current non-targeted small molecule identification pipelines. CCS is a measure of an ionized molecule's effective interaction surface with a buffer gas from ion mobility spectroscopy separations. Importantly, both properties can be consistently and accurately measured experimentally, as well as predicted computationally.

An important feature of DarkChem is its use of a 3-stage transfer learning method that enables the network to learn fundamental molecular structure representation from tens-of-millions of molecules before subsequent optimization of the network to improve its ability to predict chemical properties. This is highly valuable, as experimental chemical property training sets are often too small to take advantage of large and complex deep learning networks without risk of overfitting (e.g., trivially memorizing all, or portions, of the training set, compromising model generalizability). Thus, the training set size is able to be increased for molecular property predictors despite limited experimental data. Since m/z is trivially calculated from chemical formula/structure, there is access to ~53 million structure-m/z pairs, but without CCS, from PubChem. Additionally, the in silico Chemical Library Engine (ISiCLE) was used to generate in silico CCS for ~600 k compounds from the Human Metabolome Database (HMDB), the Universal Natural Product Database (UNPD), and the Distributed Structure-searchable Toxicity (DSSTox) database. Finally, a set of 756 experimentally validated CCS values (metabolomics.pnnl.gov) is curated from in-house data and from the literature. Through a cascade of transfer learning iterations, a network is able to learn as much as possible from each dataset, enabling success with progressively smaller datasets without overfitting. Through the training regime, DarkChem is able to predict CCS to an average error of 2.5%, which is sufficient for immediate use by the metabolomics community to help build evidence for the presence of molecules and downselect candidate structures for samples run on ion mobility-mass spectrometry instruments, as demonstrated in a small test application of a series of synthetic complex samples. Furthermore, DarkChem's generative capacity is highlighted, wherein novel molecular structures can be generated to match a set of desired experimental properties.

FIG. 1 illustrates a network schematic according to some embodiments. The network involves an encoder, a latent representation, and a decoder. Additionally, a property predictor is attached to the latent representation. For the encoder, layers include SMILES input, character embedding, and a series of convolutional layers. The latent representation is a fully connected dense layer. The decoder comprises convolutional layers, followed by a linear layer with softmax activation to yield outputs. Finally, the property predictor is a single dense layer connected to the latent representation with 20% dropout.

DarkChem was written in Python (version 3.6) and uses Keras with Tensorflow backend. Training was performed using Marianas, a cluster with Nvidia Tesla V100 (12 nm lithography, 5120 CUDA cores at 1246 MHz, 32 GB HBM2 memory) GPUs, provided by Pacific Northwest National Laboratory Research Computing.

Variational Autoencoder Architecture

The overall DarkChem architecture includes four components: 1) an encoder, including a SMILES input encoder and convolutional layers, 2) a latent space, which holds the vector representation of molecular structure, 3) a decoder, including convolutional layers and a SMILES character decoding layer, and 4) a property prediction layer. Components 1-3 comprise the VAE, which predicts inputs after encoding to a continuous numerical representation, and component 4 additionally predicts desired chemical properties, here accurate mass and CCS. FIG. 1 shows a high-level schematic of the network architecture.

The network used for autoencoding SMILES input was structured similar to the VAE introduced in Gomez-Bombarelli et al., but with several key departures. The character set used involved 38 unique alphanumeric, punctuation, and symbol characters (e.g., 'C', '1', '(', '=') representing all characters present in the datasets used, plus a "pad" character. Datasets were downselected to molecules containing only carbon, hydrogen, nitrogen, oxygen, phosphorus, and/or sulfur (CHNOPS) atoms, and SMILES string lengths of 100 characters or fewer. This downselection was motivated by the application area (small molecule identification and metabolomics), wherein structures of interest are limited to CHNOPS molecules with low molecular weight (SMILES length serves as a surrogate filter for mass, as well as to limit network input size). SMILES strings fewer than 100 characters were extended to 100 characters with the pad character.

Each character was mapped to an arbitrary, but consistent, index, realizing a vector representation of inputs, which are passed to a 32-dimensional character embedding layer. This enables the network to learn a rich representation of the character set, rather than operate on arbitrarily assigned indices. Because of this step, vector inputs are evaluated against one-hot categorical encodings, as embedding layers cast integer indices as dense vectors for use in subsequent layers of the network. Thus, although an autoencoder, Dark-Chem's inputs (index vectors) and labels (one-hot encodings) differ in their representation, but only superficially.

Three convolutional layers with [10, 10, 11] filters and kernel size [9, 9, 10], respectively, follow the character embedding, each with rectified linear unit (ReLU) activation. These connect to a linearly activated dense layer of 128 dimensions, corresponding to the latent vector representation of molecular structure. The variational components of the autoencoder are also initialized at this step as linearly activated dense layers, representing the mean and variance of the variational noise added to the latent representation. A Kullback-Leibler divergence term (Equation 1) was added to the objective function evaluation in order to penalize departures from a mean of 0 and a variance of 1, ensuring normally distributed noise was added to the latent representation during training, scaled by hyperparameter epsilon ($\square$=0.8). Left side terms are the Kullback-Leibler divergence, DKL; expected and observed probabilities q$\square$ and p$\square$, respectively, over a set of observed variables, x, and a set of latent variables, z, with joint distribution p(z, x). Right side terms are the number of samples, N; the standard deviation of the distribution, $\square$; and the mean of the distribution, $\square$.

$$D_{KL}(q_\phi(z|x)\|p_\theta(z)) = -\frac{1}{N}\sum_{i=0}^{N} 1 + \log(\sigma) - \frac{\mu^2}{2} - \sigma \qquad \text{Eq. 1}$$

The decoder connects directly to the latent dense layer and includes three convolutional ReLU layers with [10, 10, 11] filters and kernel size [9, 9, 10], respectively, as in the encoder portion of the network. Finally, a softmax-activated dense layer, reshaped to match the dimensionality of the one-hot encoded targets, was added to predict final character sequences. The softmax outputs were evaluated using categorical cross entropy (Equation 2) during training, but final outputs were decided using a beam search decoder, an algorithm that yields the k most-probable discrete string predictions from the softmax outputs produced by the network. The network was optimized by AMSGrad with default parameters except decay, which was set to 1E-8. Batch size during training was 128, following recommendations from Keskar et al., which demonstrates that networks trained using large batch sizes suffer in their ability to generalize.

Property Prediction

For multitask configurations in which labels are supplied for a semi-supervised training approach, the network additionally initializes a property prediction subnetwork that connects directly to the latent dense layer, but with 20% dropout such that property concepts are learned redundantly in the latent representation, with the intent of minimizing excess nonlinearity and overfitting. A single, linearly activated dense layer with shape equal to the number of predicted labels (arbitrary, but in this work was of dimension two: CCS and m/z) is then used for property prediction.

CCS varies among multiple ion forms, or adducts, of a single parent molecule. Based on the ISiCLE and experimental training data sets available for this work, these include protonated, [M+H]+, deprotonated, [M−H]−, and sodiated [M+Na]+ adducts, though there are many more possible adduct types. Separate networks were trained to predict CCS and m/z for each adduct type, but CCS is generally in reference to [M+H]+, unless otherwise specified.

Objective Function

DarkChem is trained via a custom objective function that minimizes categorical cross entropy (Equation 2) between softmax-activated predictions and one-hot-encoded targets, where N represents the number of observations, J the number of classes (possible characters), and y and $\square$, the observed and expected variables, respectively. Additionally, a Kullback-Leibler (KL) divergence term (Equation 1) was included in the objective function evaluation to ensure that normally distributed noise was added to the latent representation during training by penalizing departures from mean 0 and variance 1. Categorical cross entropy and KL-divergence terms are weighted equally (e.g., representations in Equations 1 and 2 were summed without scaling).

$$CCE = -\frac{1}{N}\sum_{i=0}^{N}\sum_{j=0}^{J} y_j \log(\hat{y}_j) + (1-y_j)\log(1-\hat{y}_j) \qquad \text{Eq. 2}$$

When predicting labels under a semi-supervised multitask learning configuration, a separate objective function is used to evaluate property prediction loss as the mean absolute percent error between the predicted and target property vector. Thus, the VAE loss is represented by categorical cross entropy and KL-divergence losses, while the property prediction loss, present during multitask training, is the mean absolute percent error loss of the predicted property vector. The two loss terms are weighted equally.

Figure 2:
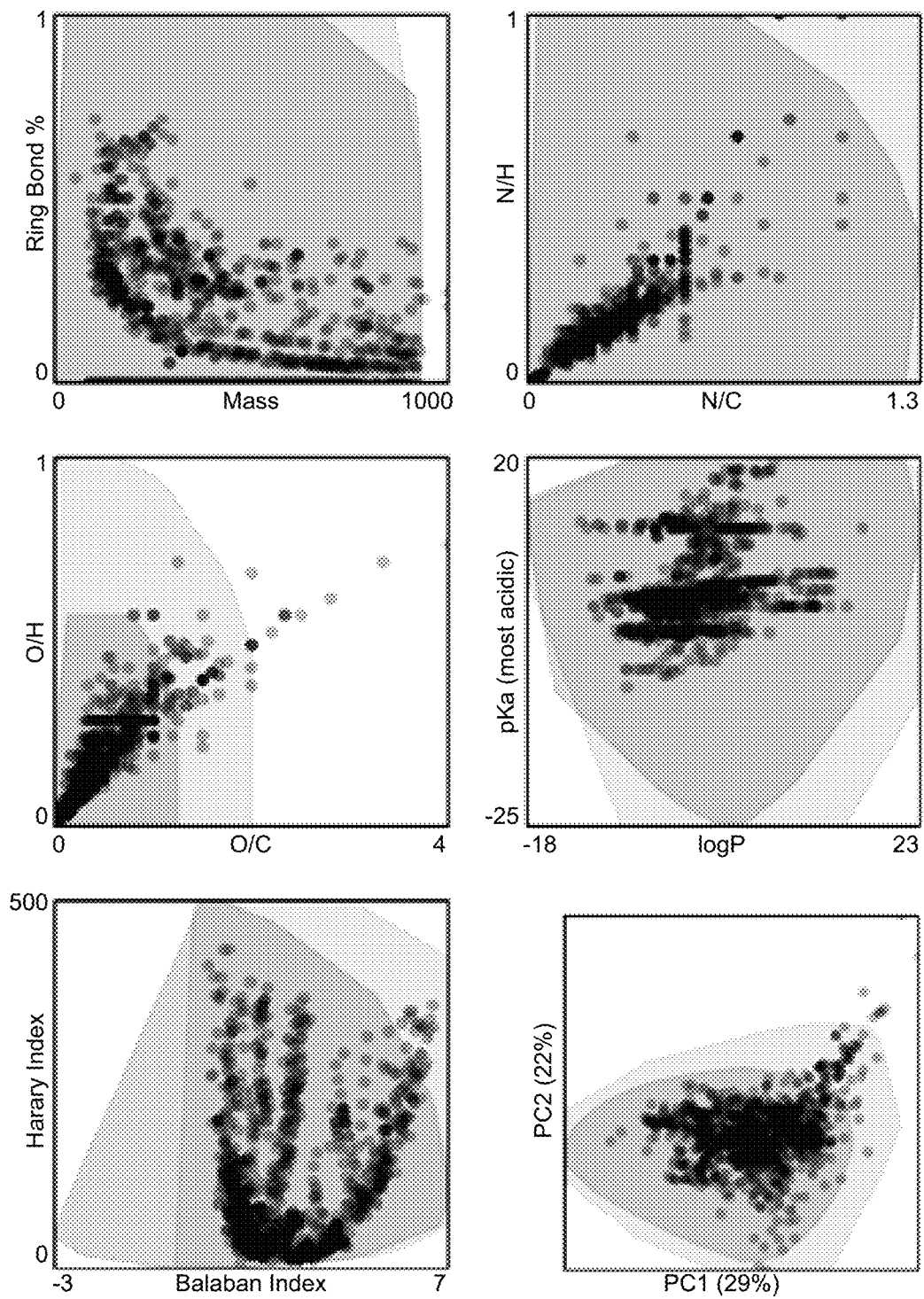
FIG. 2 illustrates a training set chemical space coverage according to some embodiments.

FIG. 2 illustrates a training set chemical space coverage according to some embodiments. The images (a) show a distribution of predicted properties. The image (b) shows principal component analysis performed on the properties plotted in (a), with properties normalized to have a mean of 0 and standard deviation of 1. The convex hull for the PubChem dataset, the convex hull for the in silico dataset, and the experimental dataset are shown. All convex hulls cover 99.5% of the underlying data.

Training

In some embodiments, three datasets are used for training: PubChem; the union of the Human Metabolome Database (HMDB), the Universal Natural Products Database (UNPD), and the Distributed Structure-Searchable Toxicity (DSSTox) database with in silico predicted CCS values, henceforth the "in silico dataset"; and a curated library of molecules with experimental CCS values (metabolomics.pnnl.gov), which span a representative subset of known chemical space. The PubChem dataset is used to pretrain the VAE on a large set of SMILES strings (N=53,335,670) with calculated m/z. The in silico data set additionally included CCS, calculated using ISiCLE. Thus, the in silico dataset is a larger (N=608,691) proxy to actual experimental CCS values (N=403, 486, and 371 for [M+H]+, [M−H]−, and [M+Na]+ adducts, respectively; a combined 756 unique parent molecules), more amenable to training a large neural network. In some embodiments, a different number of datasets are used for training, and in some embodiments other datasets are used for training.

A number of training configurations are evaluated in order to achieve success with progressively smaller datasets without overfitting. These include training directly on the small experimental dataset, training on in silico data only, and transfer learning configurations wherein the network is pretrained on PubChem and/or in silico data and subsequently "tuned" on experimental data. Transfer learning configurations also includes pretraining with VAE-only and multitask (VAE plus property) networks. Additionally, in an effort to minimize overfitting effects, particularly with tuning on the small experimental dataset, transfer learning configurations are explored wherein the VAE weights are fixed, meaning only property predictor weights could vary during training with subsequent datasets. This effectively "freezes" the latent representation of molecular structure for subsequent training steps with smaller datasets. Although many training configurations are possible, the training configuration described herein includes the network that involved: (i) train VAE and m/z predictor on PubChem, (ii) continue training on the in silico dataset, with the addition of CCS prediction, (iii) finish training the m/z and CCS predictor on experimental data, with frozen VAE weights. A schematic of the training paradigm is depicted in FIG. 3.

Figure 3:
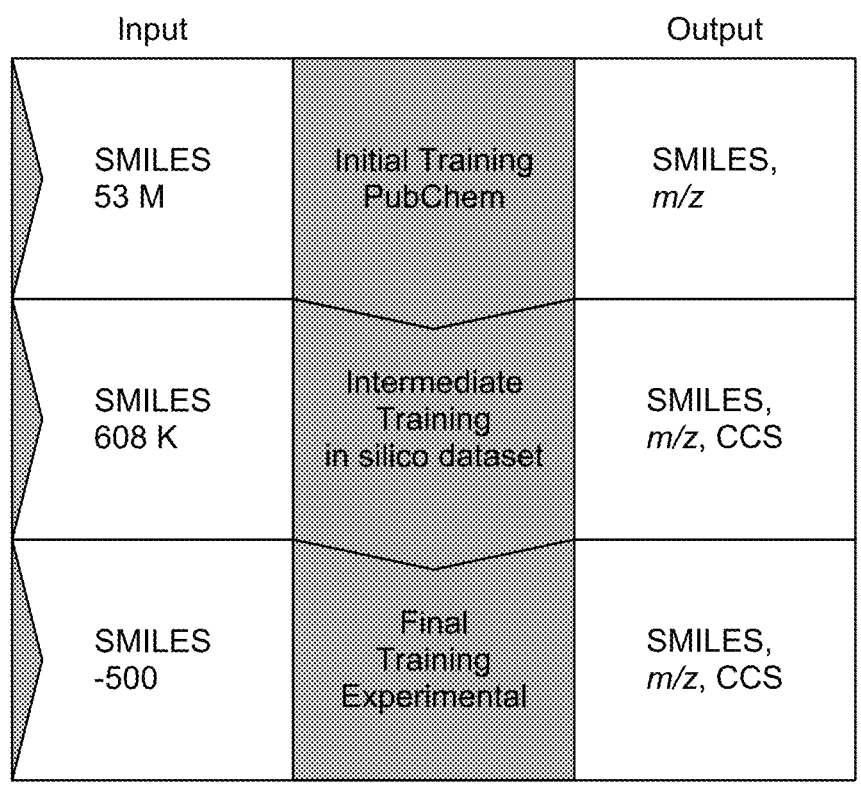
FIG. 3 illustrates a training schematic according to some embodiments.

FIG. 3 illustrates a training schematic according to some embodiments. DarkChem was initially trained on ~53 million inputs from PubChem, wherein m/z was the only predicted property. Weights from this network were used to seed the next, which involved training on the ~600,000 in silico dataset, with m/z and in silico CCS labels. The further trained weights seeded the final training step, which involved ~500 inputs with m/z and experimental CCS. For some network configurations, weights were frozen (e.g., no longer updated) to prevent overfitting to smaller datasets, in particular the experimental dataset.

Validation is performed on a random 10% subset for PubChem and the in silico dataset. For the experimental dataset, 100 iterations of repeated random subsampling validation with 10% holdout are performed, with performance metrics averaged across cross validation iterations. In some embodiments, training data is shuffled before each epoch, and training is performed for 10,000 epochs with an early stop callback (patience 1,000) to avoid overtraining.

Hyperparameter Selection

The instantiation of the network detailed here contains specific selections for all hyperparameters, but the network is architected such that all parameters are configurable through the command line. This includes character embedding dimension; number of filters, kernel sizes, and number of convolutional layers; latent dimension size; epsilon, which scales the noise added during training; and dropout fraction on the latent vector for property prediction. Additionally, several aspects of the network architecture are detected automatically, including length of input vectors, number of unique characters, and number of target labels (for multitask training). Using this generalized framework, a sweep over selected parameters, including latent dimension size, number of filters, kernel size, noise parameter epsilon, dropout, and embedding dimension, wherein each parameter was varied one at a time, is performed.

In Silico CCS Library Generation

CCS values are determined from SMILES found in the PubChem and in silico datasets (e.g., HMDB, UNPD, and DSSTox) through the trained DarkChem network to generate CCS for [M+H]+, [M−H]−, and [M+Na]+ adducts. This is done without the normally distributed noise (epsilon) added to the latent representation during training. Membership of each CCS value (N=161,965,516) is assessed whether they were inside or outside of the same chemical space as the experimental training set. This is performed by evaluating membership within the convex hull encompassing the training set in the first eight dimensions from the principal component analysis (PCA) of DarkChem's latent space. Those found within the chemical space are included as entries into the final in silico CCS library (N=90,995,413).

Beam Search Decoder

A beam search decoder is able to be implemented to realize k discrete strings from softmax predictions, where k is the beam width, yielding the k most probable SMILES sequences. Thus, beam search may be used for all generative applications, offering several advantages over the argmax operator.

Generative Mode

When using the network in a generative capacity for inverse QSPR, the desired outcome involves predicting candidate structures from known property signatures (e.g., CCS, m/z) obtained from experimental instruments (e.g., ion mobility spectroscopy, mass spectroscopy). The training paradigm used enables effective entanglement without excessive nonlinear overfitting such that PCA is able to project the latent representation into a space that correlates, in at least one dimension, with desired properties. Thus, one can start with a molecule of a certain m/z and CCS and move orthogonally to the respective correlated PCA dimension(s) to yield putative structures with shared property information. PCA is performed using scikit-learn, and correlation with desired properties is evaluated using the correlation coefficient between each principal component and each property. Latent shaping is considered successful when (i) at least one principal component correlated heavily with predicted properties, and (ii) at least one principal component is invariant to (or uncorrelated with) predicted properties. With (i) and (ii) satisfied, putative structures are generated by moving in the dimension(s) defined by (ii) and subsequently performing the inverse transform on the PCA vector to yield a latent vector representation. Resulting latent vectors are decoded using beam search and additionally checked to ensure they mapped to valid SMILES strings using rdkit.

Synthetic Complex Samples and Analytical Experiments

Samples were provided through the U.S. Environmental Protection Agency—Non-Targeted Analysis Collaborative Trial (ENTACT) challenge, a blinded inter-laboratory challenge, designed for the objective testing of non-targeted analytical chemistry methods using a consistent set of synthetic mixtures. Each mixture contained between 95 and 365 compounds, all selected from the EPA ToxCast chemical library. The ten synthetic mixtures and blanks were analyzed using a drift tube ion mobility spectrometry-mass spectrometer, and a 21-Tesla Fourier transform-ion cyclotron resonance spectrometer-mass spectrometer (FTICR-MS) in both positive (+) and negative (−) ionization modes. Evidence for the presence of molecules in each sample was assessed using the Multi-Attribute Matching Engine (MAME), a modular Python package that performs feature downselection and a weighted scoring system that, in the case of the ENTACT study, was used to assign compounds as suspected present if their score surpassed a defined threshold. Any compounds labeled as suspected present that, after unblinding, were found to be intentionally spiked in are considered as true positives.

Results and Discussion

Motivation for the VAE network configuration was multifaceted: (i) VAEs are useful as property prediction frameworks, (ii) a VAE could improve upon existing methods—both first-principles simulation and other machine-learning based approaches—in terms of accuracy and throughput, and (iii) VAEs can be used in a generative capacity for QSPR. That is, a VAE learns a continuous numerical, or latent, representation of molecular structure (and associated properties) such that novel candidate structures with desired properties can be generated for use in untargeted metabolomics and small molecule identification applications. The multitask training configuration was designed to coax the network into encoding molecular properties explicitly, despite being emergent properties of structure, without supplying this information directly (e. g., encoding through prediction rather than via input). Thus, results are interpreted in both capacities: the network as a property predictor and the network as a generative tool for small molecule identification and discovery. Additionally, the value added by performing this training simultaneously is assessed, as synergistic effects of combining an autoencoder with property prediction are demonstrated.

Reconstruction Accuracy

Although not explicit in the objective loss, reconstruction accuracy, the mean per-character absolute difference between input and predicted SMILES sequences, was used as an intuitive performance assessment. The network trained on the limited (N=403 for [M+H]+ adducts) experimental data only yielded validation reconstruction accuracy of 78.5%. This is in contrast to the transfer learning (final production-mode) network, which achieved validation reconstruction accuracy of 98.9% for the experimental dataset and 99.0% for the in silico dataset, indicating that a sizeable and varied dataset is important to learn a general representation of chemical structure. Out-of-sample validation (network trained on experimental values only, evaluated with in silico data) further confirmed this discrepancy, as reconstruction accuracy was only 70.8% with out-of-sample data. Thus, the power of the 3-stage transfer learning method is confirmed, taking advantage of much larger training sets than is typically possible, compared to traditional single stage learning approaches. It is worth noting that reconstruction accuracy, though integral to the success of training a VAE, is only a proxy for the true objective of the network. Reconstruction accuracy represents the network's ability to recreate an input SMILES string from its associated latent representation, despite added noise. The added noise ensures the latent space is continuous, rather than discrete per each entry in the dataset, but at what point should a noise perturbation yield a new structure? Moreover, during training, if the added noise does yield a new structure, the network is penalized as said structure does not match the input. This is antithetical to the goal of the VAE, as it functions to generate new structures from a given input following perturbation, yet is penalized during training when this occurs. When considering the network in a generative capacity, adding noise to a known latent vector should, with sufficient noise magnitude, yield a new, valid SMILES structure, not the input. Still, training a VAE, which attempts to faithfully recreate inputs despite added noise, functions as a reasonable proxy to a valid SMILES discriminator, as evidenced by the ability of the networks trained on in silico data to generalize to out-of-sample experimental data, with and without experimental fine tuning.

Property Prediction

The use of a shared latent space is important. That is, a latent space that simultaneously encodes a continuous numerical representation of structure and associated chemical properties. Coupled with the use of a relatively small (with respect to number of layers) property decoder, which forces the latent space to encode this chemical property information, the resulting latent representation learned a rich representation.

In most cases, networks are able to achieve reasonable success when predicting in-sample CCS and m/z. Training on experimental data only, validation error was 3.5% and 2.2% for CCS and m/z, respectively. The best performing network in terms of CCS prediction achieved CCS and m/z errors of 2.5% and 0.7%, respectively. The final transfer learning configuration, selected for its advantages in generality and latent space correlations, had validation error of 3.0% and 0.4% for CCS and m/z, respectively. Although some of the focus is on CCS for [M+H]+ adducts, networks were additionally trained to predict [M−H]− and [M+Na]+, each with comparable reconstruction accuracy (99.3% and 99.5%, respectively), m/z prediction error (0.4% and 0.3%, respectively), and CCS error (3.1% and 2.5%, respectively).

The network's capacity to predict properties directly from chemical structures (as represented by canonical SMILES strings) represents a new tool for the metabolomics and small molecule identification community, particularly concerning the prediction of CCS (m/z is important for using the network in a generative capacity, but this property is trivial to calculate otherwise). Previous efforts have been able to achieve 3.2% error using first-principles simulation and 3.3% error via property-based machine learning approaches, and 3.0% error via a non-generative, SMILES-based deep-learning approach, each evaluated on the experimental data. The method described herein uses structure, represented by SMILES string, to predict properties directly, and is able to do so with lower CCS error for most adducts. Additionally, prediction time (after training) is orders of magnitude faster than first-principles simulation (milliseconds on a laptop compared to node-hours on a high performance computer), and does not require chemical property calculation needed for use with property-based methods, such as MetCCS. Finally, DarkChem is a generative approach, enabling usefulness beyond just property prediction. With consideration to accuracy and computational efficiency of this method, it emerges as a highly useful tool for in silico chemical property library expansion for applications in standards-free small molecule identification and metabolomics.

Property Correlation

Figure 4:
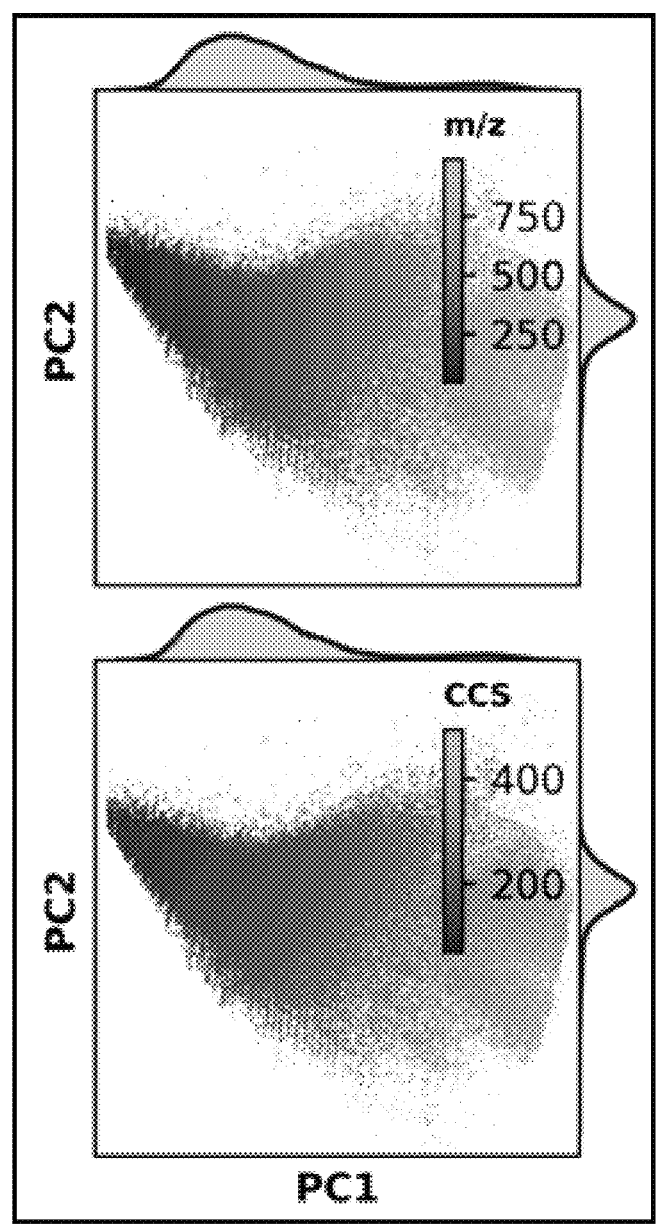
FIG. 4 illustrates a diagram of latent space according to some embodiments.

The property "concepts" learned by the network through supervised prediction were evaluated in terms of how select dimensions of the latent representation were correlated—and uncorrelated—with m/z and CCS. Correlation analysis was also performed in PCA space. Properties were plotted against the most and least correlated latent dimensions, as well as the most correlated PCA dimension. Important to this analysis was the fact that dimensions, to some degree, specialize in human-interpretable information (e.g., the prediction of chemical properties), as indicated by different latent dimensions correlating most heavily with m/z and CCS, respectively, as well as multiple dimensions exhibiting no correlation with predicted properties, presumably specializing in other network concepts. Further elucidation of human-interpretable network concepts learned during training is a target for future effort. Additionally, the first principal component exhibited even greater correlation with m/z and CCS than any individual latent dimension (FIG. 4). Thus, moving along those remaining principal components uncorrelated with m/z and CCS proved useful for QSPR applications, wherein putative structures could be yielded for a given m/z and CCS. Traversing dimensions invariant to m/z and CCS enables generation of known and potentially novel candidates that can be matched to currently unannotatable—due to lack of authentic reference values—experimental signals.

FIG. 4 illustrates a diagram of latent space according to some embodiments. The first two principal components of the 128-dimensional representation are shown, colored by predicted property value (top: m/z, bottom: CCS). The representation is a 2D binned statistic of the mean, with grid size 384 in each principal component dimension. A kernel density estimator is also shown for each principal component dimension, emphasizing density of the distribution. Clear correlations to m/z and CCS are observed, largely across the first principal component.

Training Paradigm

Although only a select few of the networks evaluated were useful for generative applications (QSPR, interpolation) and/or property prediction, the poorly performing networks revealed several interesting insights. Reconstruction accuracy was low when training on experimental values directly, thus causing use of the in silico dataset and/or the PubChem dataset, as each were of sufficient size to yield satisfactory reconstruction accuracy and property prediction error, if applicable. However, as evidenced by the high property prediction error in networks seeded with the frozen autoencoder weights of the PubChem-trained networks, high reconstruction accuracy did not indicate a representation of molecular structure sufficient for m/z and CCS prediction. Thus, the intermediate step of training on in silico data allowed property concepts to form in the latent representation, and also enabled the weights of the autoencoder portion to be frozen during training on the small experimental dataset to avoid overfitting. Although it was possible to achieve high reconstruction accuracy and low property prediction error training on just the in silico dataset followed by the experimental dataset, the learning configurations that included PubChem were preferred to include a larger number of varied training examples, particularly considering that the experimental data is completely subsumed by the in silico dataset, but PubChem contains molecules outside the in silico dataset (based on convex hull analysis). This indicates that networks trained with PubChem data would generalize favorably to molecules in this region, compared to those trained without.

Chemical Space Coverage

Given the potentially rich representation of chemical structure encoded in each latent vector, categorizations in terms of dataset and chemical class were performed in principal component space for visual interpretation. For dataset source, convex hulls were constructed for each of PubChem, HMDB, UNPD, and DSSTox, as well as the convex hull of their union, and plotted. Datasets largely overlapped, but some spanned distinct regions of the PCA representation. Notably, the HMDB, which was the only dataset containing a high number of lipids—structures with high m/z and CCS—was also the only dataset to occupy the rightmost portion of the PCA convex hull. Similarly, PubChem was the only dataset with a non-biological focus; it thus spanned the largest portion of the PCA representation of latent space, particularly unique in its coverage of the leftand upper-most portions. Similar analysis was performed for chemical class (defined by ClassyFire). Hull separations were distinctly visible for several classes, while others depicted regions of significant overlap, indicating the latent representation encoded, in at least some capacity, a distinction among molecules from human-assigned ontology.

In Silico Library

DarkChem was used to generate CCS predictions for a set of 3 adducts for molecules from PubChem, HMDB, UNPD, and DSSTox. CCS values for [M+H]+, [M−H]−, and [M+Na]+ adducts are made available in the SI (and will be kept updated at metabolomics.pnnl.gov). To ensure conservative predictions, that is, only predicting values for molecules similar to those in the experimental training set, a convex hull of the experimental data was constructed from their associated latent vectors. Compounds from PubChem, HMDB, UNPD, and DSSTox that fell within the convex hull of experimental values were used to build the library, which currently contains 90,995,413 entries, and is being updated as more data becomes available.

Analysis of Synthetic Complex Samples

Evidence has been found for 618 true positive compounds that were suspected present from analysis using MAME. Calculated CCS from ISiCLE increased the confidence of 84% of molecules that were correctly determined to be present in the samples, showcasing its importance as an additional property to mass and isotopic signatures. Compared to the true positive experimental standards spiked in these samples that were uniquely identified, calculated CCS errors for DarkChem values was 2.8% and 2.6%, for those CCS that fell within the same latent space as the experimental training set (N=37), or outside (N=25), respectively. This is comparable to 3.2% error when using ISiCLE CCS values, as were originally used in the study, and a 2.9% error when using DeepCCS. This out-of-sample test demonstrates consistent CCS error values compared to the initial validation set.

Generative Modes

Figure 5:
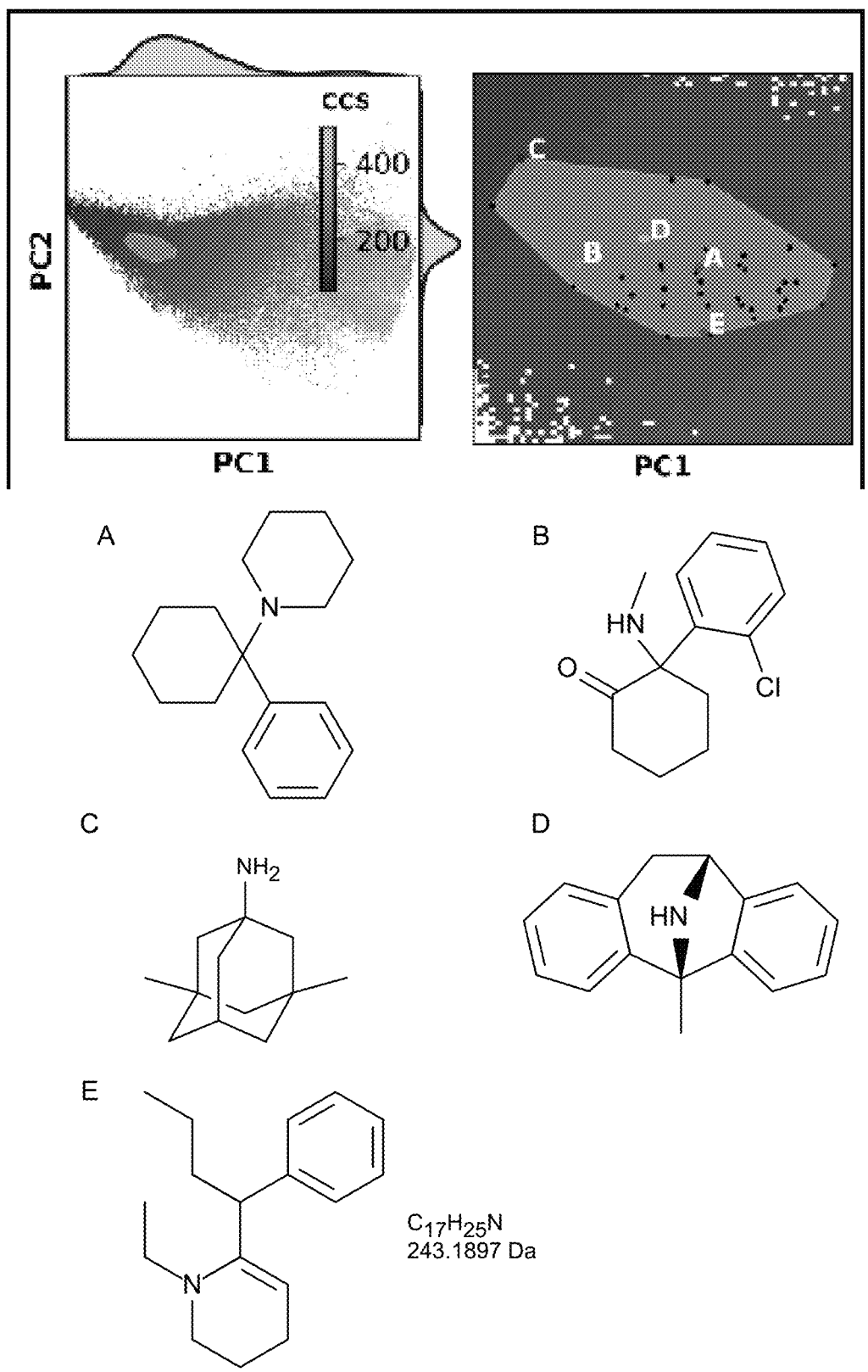
FIG. 5 illustrates a diagram of known NMDA receptor antagonists (A-D) as they map to a 2D representation of latent space, as well as a novel generated molecule with desired properties (E) derived from sampling latent space.

The network resulting from the cascade of transfer learning iterations was used in two generative applications: first, an interpolation between adenine and cholesterol and second, generation of a putative compound analogous to a set of known PCP analogues, with a specifically targeted m/z and CCS value (FIG. 5).

FIG. 5 illustrates a diagram of a NMDA receptor antagonists according to some embodiments. By seeding latent space with a known set of NMDA receptor phencyclidine (PCP) site antagonists (shown: a. phencyclidine, b. ketamine, c. memantine, d. dizocilpine), a large number of putative PCP analogues were yielded. Of these, a novel analogous structure (e), 3-{8,9-dihydro-5H-benzo[7]annulen-1-yl}-2-propylazetidine, was found with 5 ppm mass error and 0.2% error in predicted CCS (experimental CCS not evaluated).

For interpolation, a direct linear interpolation—that is, projecting a vector from the latent representation of molecule A to the latent representation of molecule B and sampling along its length—caused sampling of empty regions of latent space, meaning interpolated latent vectors decoded to invalid SMILES strings in some cases. To ameliorate this phenomenon, the closest training example to each interpolated point along the interpolation vector was used to seed a number of putative structures. From these sets, molecules were selected to minimize the standard deviation of latent space distance between each interpolate. This was in an attempt to produce a set with as-smooth-aspossible transitions. These empty regions of latent space represent a shortcoming of the network, which will be addressed in future efforts.

For analogue generation, an initial set of known N-methyl-D-aspartate (NMDA) receptor PCP site antagonists was used to seed a subregion of latent space. The mean and standard deviation of the latent representations of these known antagonists were used to sample a normal distribution to yield putative analogues. The putative list was filtered by m/z and CCS error to find candidates closely resembling PCP in their property signature. The most similar novel structure is shown in FIG. 5, with m/z error of 5 ppm (calculated from formula), and predicted CCS error of 0.2%, as well as the clustering of the known NMDA receptor antagonists in latent space (compressed to two dimensions by PCA).

Figure 6:
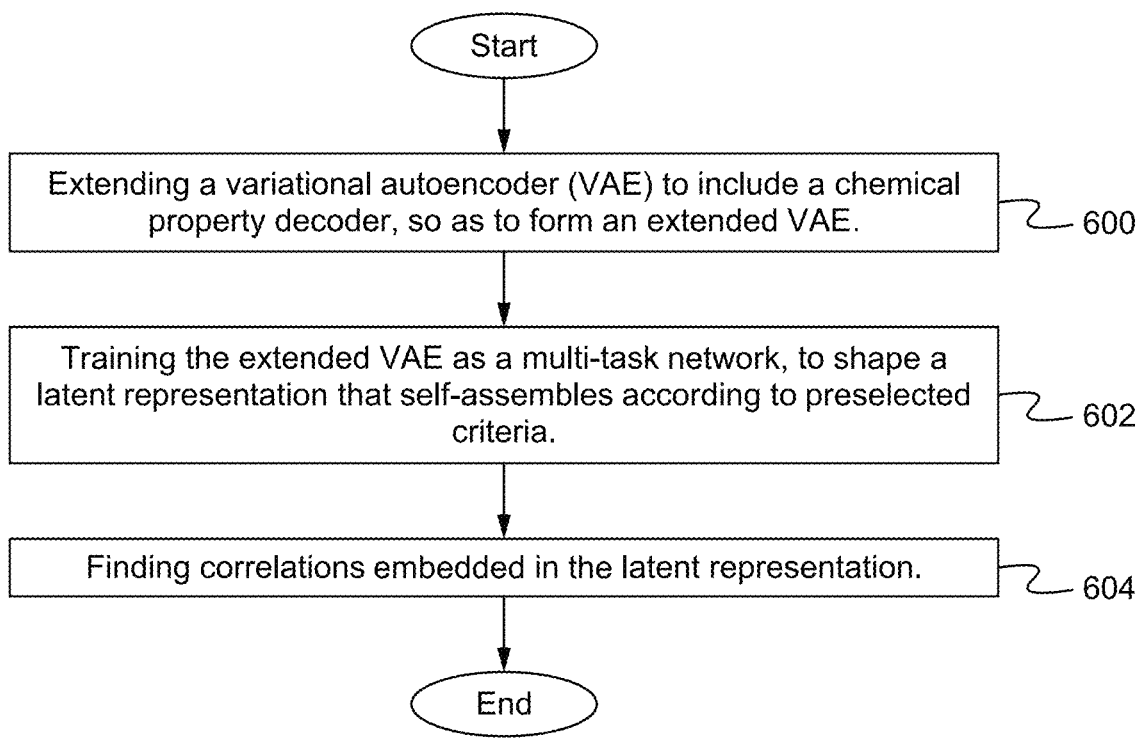
FIG. 6 illustrates a flowchart of a simultaneous characterization and expansion method according to some embodiments.

FIG. 6 illustrates a flowchart of a simultaneous characterization and expansion method according to some embodiments. In the step 600, a variational autoencoder (VAE) is extended to include a chemical property decoder and/or any other additional components, so as to form an extended VAE.

In the step 602, the extended VAE is trained as a multi-task network, to shape a latent representation that self-assembles according to preselected criteria. In some embodiments, training includes processing a cascade of transfer learning iterations including: first, a large dataset of unlabeled structures, second a dataset of properties calculated in silico and third a dataset of limited experimental data for fine tuning. In some embodiments, the first layer of training includes receiving in silico data or large datasets related to properties of interest which allows network to learn general concepts and then apply general concepts to a specific problem.

For example, training starts with any number (e.g., approximately 50 million) of molecular structures from public or private databases or other sources. This first training set is used to teach a system what a molecule is so that the system learns concepts such as bonding rules (what type of atoms can be bonded to each other and types of bonds, how many bonds). The weights learned during training are used as the initial conditions for the second layer/training. In the second layer of training, another number (e.g., approximately 600,000 structures) are input and analyzed, where the molecular bonding structure, mass, calculated collision cross section, and/or other characteristics for the structures are known. In the third layer of training, the system is introduced to experimental datasets. In some embodiments, each layer outputs weights and/or other data to be used in characterizing/classifying structures and/or characteristics In some implementations, all the weights from the first two training layers are frozen, except for one layer that was used for calculating chemical properties, which enables calibration for experimental values.

In the step 604, correlations are found embedded in the latent representation. The correlations embedded in the latent representation enable prediction of chemical properties from structures generated along manifolds defined by chemical property analogues. After training, the method and system are able to receive a structure as an input and provide one or more properties of the structure as an output, or receive one or more properties as an input and provide one or more structures as an output.

In some embodiments, the order of the steps is modified. In some embodiments, fewer or additional steps are implemented.

In some embodiments, character embedding is implemented including learning the relationships among different characters or symbols that are used to represent molecular structure (e.g., as in SMILES or InChI molecular structure representations). From that, clustering of different types of atoms that are associated and different types of bonds are able to be determined.

In some embodiments, a beam search is implemented which enables the vector representation of a structure to be converted back into multiple, most-probable full structures. This allows a user to sample the latent representation for new molecules that have not been found before (e.g., change an oxygen to a nitrogen or carbon single bond to carbon double bond).

In some embodiments, the input is just the molecular structure itself without any additional information, and then the system predicts the properties based on the input structure. In some embodiments, the inputting one or more properties to determine a molecular structure is implemented. The system is able to perform both operations.

In some embodiments, the system is changed to implement a global attention mechanism which informs a user why certain chemical bonds are giving certain properties (e.g., input a molecular structure and the system outputs why the structure has certain properties, or vice versa, input certain properties and the system outputs a molecular structure and why the certain bonds are made).

In some embodiments, the system is changed to implement a molecular structure discriminator which is an added deep learning network that determines whether a structure is both syntactically and chemically valid (e.g., output structures are automatically assessed for validity and rejected if invalid).

In some embodiments, the system is changed to implement a molecular structure discriminator which is used to modify the training loss function during training of the VAE, such that the latent space would be penalized for and therefore be trained to avoid creating structures that have physically/chemically invalid bonding types, molecular topologies, and/or nonbonding interactions.

In some embodiments, the system is changed to implement a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which would therefore iteratively improve the percent of valid structures that the VAE produces and increase the discrimination power of the structure discriminator.

In some embodiments, the system is able to move beyond chemical property predictions for mass spectrometry and go to properties or features derived from nuclear magnetic resonance, chromatography and other liquid-phase separation methods (e.g., precipitation, extraction, including solid phase extraction, and distillation), advanced ion mobility and other gas-phase separation methods, electroanalytical/electrochemical methods, electrophoresis, infrared spectroscopy, electron diffraction, microscopy and other photon-based instruments, analytical instruments (some which are yet to be developed) that rely on fundamental forces including and beyond electromagnetic forces (e.g., gravitation, weak or strong nuclear fundamental forces), and other analytic instrument techniques that measure chemical properties or interactions for small molecule research.

In some embodiments, the system is changed to include the encoding (e.g. mapping) of chemical and enzymatic reactions in the latent space such that novel molecules can be found by starting with known molecules and following mapped reactions to discover new molecules. These new molecules may represent real previously-unknown molecules that can be biologically- or chemically-derived through known reactions.

Briefly, known chemical reactions (e.g., known biotic and abiotic reactions; metabolic pathway ontologies from online databases such as MetaCyc) would be mapped onto latent space, and new molecules would be generated following these patterns into new latent space locations. The appeal to this approach is that chemical reaction "math" within latent space could be possible by defining reaction vectors. As a possible example, theobromine minus caffeine (representing the demethylation reaction) plus ethyltheophylline (T-C+E) could result in the latent space location of demethylated ethyltheophylline (i.e., 7-ethyl-3-methyl-3,7-dihydro-1H-purine-2,6-dione). In this manner, new molecules that are chemically possible through known reactions could reduce the massive search space and result in high probability structures that result from existing biological, biogeochemical, and industrial processes. To be more specific, a mapped chemical reaction product vector is found by adding (or other arithmetic or mathematical transformations) the reaction vector to a reactant vector. The product vector provides the location of the product molecule in latent space, which can subsequently be decoded into a structure representation. Generally speaking, a reaction vector may be calculated by taking a product vector and subtracting its reactant vector. However, the reaction vector used to predict chemical products may be the average of a list of reaction vectors under the condition of the same reaction type. For example, suppose there are 10 chemical reduction reactions, from carbon-carbon double bond to single bond. Each reaction vector is computed first, and then the 10 calculated vectors are averaged as the prediction reaction vector. The reason why average reaction vectors may be selected is obvious, as an average reaction vector enables achieving better product predictions compared to a random single reaction vector with the premise of an equal reaction type. This process of averaging and performing mathematical operations on known reaction-product pairs and their latent space vectors is used to map the reactions onto latent space. In some cases, searching around the latent space volume dictated by a mapped reaction may result in similar novel molecule compounds and can be used to fill chemical space with related molecules, including those that may arise from chemical side reactions.

Figure 7:
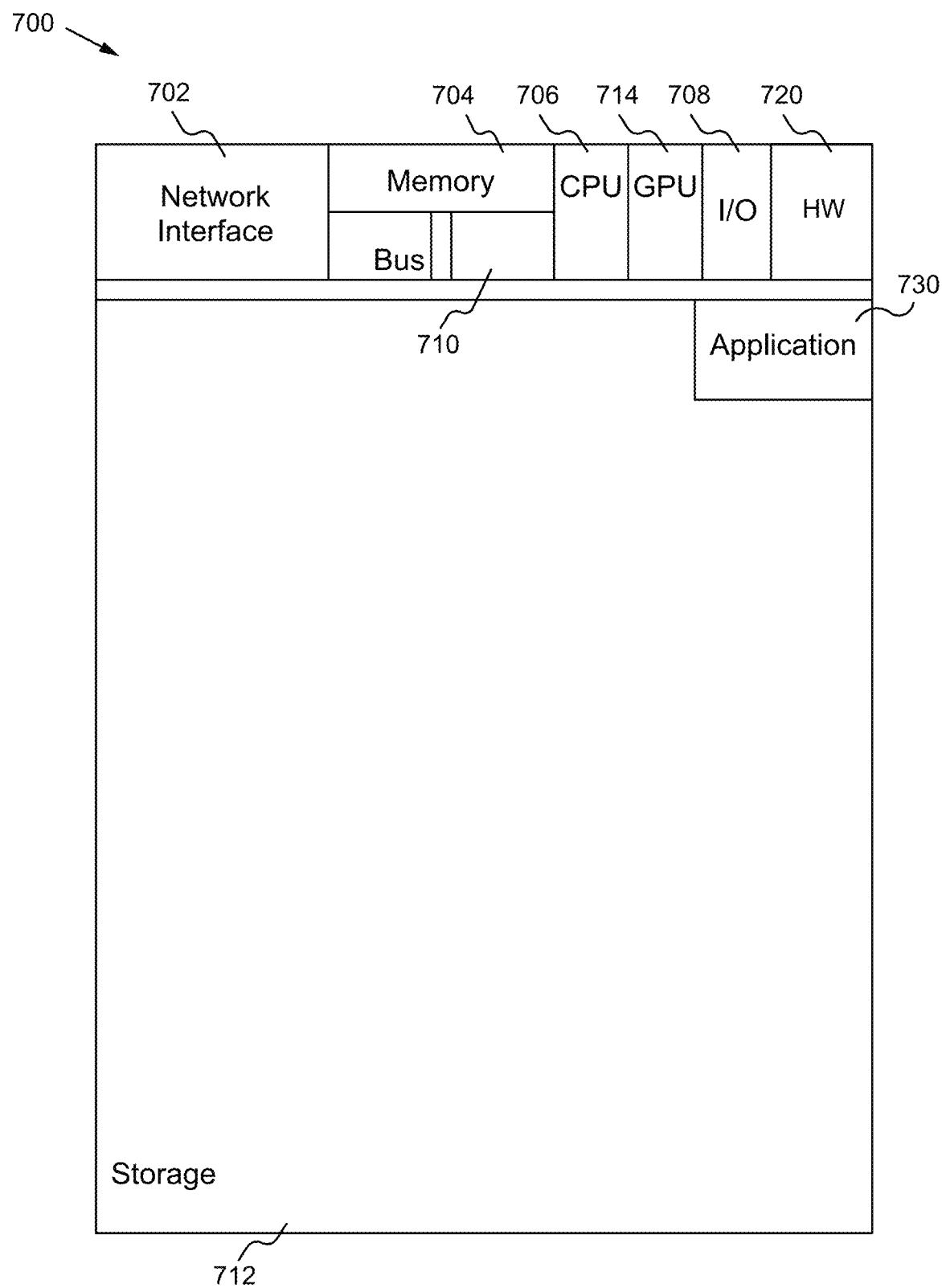
FIG. 7 illustrates a block diagram of an exemplary computing device configured to implement the simultaneous characterization and expansion method according to some embodiments.

FIG. 7 illustrates a block diagram of an exemplary computing device configured to implement the simultaneous characterization and expansion method according to some embodiments. The computing device 700 is able to be used to acquire, store, compute, process, communicate and/or display information. The computing device 700 is able to implement any of the simultaneous characterization and expansion aspects. In general, a hardware structure suitable for implementing the computing device 700 includes a network interface 702, a memory 704, a processor 706, I/O device(s) 708, a bus 710, a storage device 712, and a Graphics Processing Unit (GPU) 714. The choice of processor is not critical as long as a suitable processor with sufficient speed is chosen. The memory 704 is able to be any conventional computer memory known in the art. The storage device 712 is able to include a hard drive, CDROM, CDRW, DVD, DVDRW, High Definition disc/drive, ultra-HD drive, flash memory card or any other storage device. The computing device 700 is able to include one or more network interfaces 702. An example of a network interface includes a network card connected to an Ethernet or other type of LAN. The I/O device(s) 708 are able to include one or more of the following: keyboard, mouse, monitor, screen, printer, modem, touchscreen, button interface and other devices. Simultaneous characterization and expansion application(s) 730 (e.g., DarkChem) used to implement the simultaneous characterization and expansion method are likely to be stored in the storage device 712 and memory 704 and processed as applications are typically processed. More or fewer components shown in FIG. 7 are able to be included in the computing device 700. In some embodiments, simultaneous characterization and expansion hardware 720 is included. Although the computing device 700 in FIG. 7 includes applications 730 and hardware 720 for the simultaneous characterization and expansion method, the simultaneous characterization and expansion method is able to be implemented on a computing device in hardware, firmware, software or any combination thereof. For example, in some embodiments, the simultaneous characterization and expansion applications 730 are programmed in a memory and executed using a processor. In another example, in some embodiments, the simultaneous characterization and expansion hardware 720 is programmed hardware logic including gates specifically designed to implement the simultaneous characterization and expansion method.

In some embodiments, the simultaneous characterization and expansion application(s) 730 include several applications and/or modules. In some embodiments, modules include one or more sub-modules as well. In some embodiments, fewer or additional modules are able to be included.

Examples of suitable computing devices include a supercomputer, a personal computer, a laptop computer, a computer workstation, a server, a mainframe computer, a handheld computer, a personal digital assistant, a cellular/mobile telephone, a smart appliance, a gaming console, a digital camera, a digital camcorder, a camera phone, a smart phone, a portable music player, a tablet computer, a mobile device, a video player, a video disc writer/player (e.g., DVD writer/player, high definition disc writer/player, ultra high definition disc writer/player), a television, a home entertainment system, an augmented reality device, a virtual reality device, smart jewelry (e.g., smart watch), a vehicle (e.g., a self-driving vehicle) or any other suitable computing device. In some embodiments, the simultaneous characterization and expansion method is distributed over multiple devices (e.g., a set of supercomputers).

To utilize the simultaneous characterization and expansion method, a device/system acquires or receives input. For example, a device/system receive data for multiple levels of training. Once trained, the device/system is able to receive input such as a molecular structure and outputs molecular properties/characteristics, or receives molecular properties/characteristics and outputs a molecular structure. The simultaneous characterization and expansion method is able to be implemented with user assistance or automatically without user involvement.

In operation, a framework (e.g., DarkChem) for the characterization of small molecules that can be used for putative identifications in complex mixtures directly from experimental signals, such as m/z from mass spectrometry and CCS from ion mobility spectrometry has been described. DarkChem offers a number of advancements over previous works in that 1) properties are predicted directly from structure, as opposed to calculated chemical properties or other derived features, 2) predicted properties are relevant to the field of metabolomics, particularly for applications involving putative identifications using untargeted IMS/MS pipelines, and 3) the network was trained on the largest dataset to-date, improving learned molecular concepts and property predictions with each successive dataset (PubChem, in silico, experimental). Combined, these advances position the framework (e.g., DarkChem) as a highly useful offering in the metabolomics community and beyond, particularly considering that the framework supports training with arbitrary properties. That is, in addition to, or instead of, m/z and CCS, to meet the requirements of putative identifications from experimental data acquisitions involving varying instrument arrays.

The simultaneous characterization and expansion method involves three aspects, a network architecture which includes how the layers are set up and connected, a trained network which is able to generate a list of weights (arrays of numbers) that make the architecture useful, and output from the network which is usable for practical applications such as national security (e.g., detection of chemical weapons), biomedical research, drug discovery, small molecule metabolite detection, and many other applications.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of simultaneous characterization and expansion of reference libraries for small molecule identification comprising:
   extending a variational autoencoder (VAE) to include a chemical property decoder, so as to form an extended VAE,
   training the extended VAE as a multi-task network, to shape a latent representation that self-assembles according to preselected criteria, and
   finding correlations embedded in the latent representation, wherein the correlations embedded in the latent representation enable prediction of chemical properties from structures generated along manifolds defined by chemical property analogues.

2. The method of claim 1 wherein training includes processing a cascade of transfer learning iterations comprising: a first dataset of unlabeled structures, a second dataset of properties calculated in silico and a third dataset of limited experimental data for fine tuning.

3. The method of claim 2 wherein the first dataset is larger than the second dataset, and the second dataset is larger than the third dataset.

4. The method of claim 2 wherein an output of processing the cascade of transfer learning iterations comprises a set of weights.

5. The method of claim 1 wherein the correlations embedded in the latent representation enable prediction of the structures from the chemical properties.

6. The method of claim 1 further comprising implementing character embedding to learn relationships among different characters or symbols that are used to represent molecular structure.

7. The method of claim 1 further comprising implementing a beam search to enable the vector representation of a structure to be converted back into multiple, most-probable full structures.

8. The method of claim 1 further comprising implementing a global attention mechanism which informs a user why certain chemical bonds are giving certain properties.

9. The method of claim 1 further comprising implementing a molecular structure discriminator which is an added deep learning network that determines whether a structure is both syntactically and chemically valid.

10. The method of claim 1 further comprising implementing a molecular structure discriminator which is used to modify a training loss function during training of the VAE, such that the latent space would be penalized for and therefore be trained to avoid creating structures that have physically/chemically invalid bonding types, molecular topologies, and/or nonbonding interactions.

11. The method of claim 1 further comprising implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

12. An apparatus comprising:
    a memory configured for storing an application, the application configured for:
        extending a variational autoencoder (VAE) to include a chemical property decoder, so as to form an extended VAE,
        training the extended VAE as a multi-task network, to shape a latent representation that self-assembles according to preselected criteria, and
        finding correlations embedded in the latent representation, wherein the correlations embedded in the latent representation enable prediction of chemical properties from structures generated along manifolds defined by chemical property analogues; and
    a processor configured for processing the application.

13. The apparatus of claim 12 wherein training includes processing a cascade of transfer learning iterations comprising: a first dataset of unlabeled structures, a second dataset of properties calculated in silico and a third dataset of limited experimental data for fine tuning.

14. The apparatus of claim 13 wherein the first dataset is larger than the second dataset, and the second dataset is larger than the third dataset.

15. The apparatus of claim 13 wherein an output of processing the cascade of transfer learning iterations comprises a set of weights.

16. The apparatus of claim 12 wherein the correlations embedded in the latent representation enable prediction of the structures from the chemical properties.

17. The apparatus of claim 12 wherein the application is further configured for implementing character embedding to learn relationships among different characters or symbols that are used to represent molecular structure.

18. The apparatus of claim 12 wherein the application is further configured for implementing a beam search to enable the vector representation of a structure to be converted back into multiple, most-probable full structures.

19. The apparatus of claim 12 wherein the application is further configured for implementing a global attention mechanism which informs a user why certain chemical bonds are giving certain properties.

20. The apparatus of claim 12 wherein the application is further configured for implementing a molecular structure discriminator which is an added deep learning network that determines whether a structure is both syntactically and chemically valid.

21. The apparatus of claim 12 wherein the application is further configured for implementing a molecular structure discriminator which is used to modify a training loss function during training of the VAE, such that the latent space would be penalized for and therefore be trained to avoid creating structures that have physically/chemically invalid bonding types, molecular topologies, and/or nonbonding interactions.

22. The apparatus of claim 12 wherein the application is further configured for implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

23. A system comprising:
a first device for storing training data; and
a second device configured for:
extending a variational autoencoder (VAE) to include a chemical property decoder, so as to form an extended VAE,
training the extended VAE as a multi-task network using the training data, to shape a latent representation that self-assembles according to preselected criteria, and
finding correlations embedded in the latent representation, wherein the correlations embedded in the latent representation enable prediction of chemical properties from structures generated along manifolds defined by chemical property analogues.

24. The system of claim 23 wherein training includes processing a cascade of transfer learning iterations comprising: a first dataset of unlabeled structures, a second dataset of properties calculated in silico and a third dataset of limited experimental data for fine tuning.

25. The system of claim 24 wherein the first dataset is larger than the second dataset, and the second dataset is larger than the third dataset.

26. The system of claim 24 wherein an output of processing the cascade of transfer learning iterations comprises a set of weights.

27. The system of claim 23 wherein the correlations embedded in the latent representation enable prediction of the structures from the chemical properties.

28. The system of claim 23 wherein the second device is further configured for implementing character embedding to learn relationships among different characters or symbols that are used to represent molecular structure.

29. The system of claim 23 wherein the second device is further configured for implementing a beam search to enable the vector representation of a structure to be converted back into multiple, most-probable full structures.

30. The system of claim 23 wherein the second device is further configured for implementing a global attention mechanism which informs a user why certain chemical bonds are giving certain properties.

31. The system of claim 23 wherein the second device is further configured for implementing a molecular structure discriminator which is an added deep learning network that determines whether a structure is both syntactically and chemically valid.

32. The system of claim 23 wherein the second device is further configured for implementing a molecular structure discriminator which is used to modify a training loss function during training of the VAE, such that the latent space would be penalized for and therefore be trained to avoid creating structures that have physically/chemically invalid bonding types, molecular topologies, and/or nonbonding interactions.

33. The system of claim 23 wherein the second device is further configured for implementing a molecular structure discriminator that is trained simultaneous to the VAE with an external structure discriminator, such that the latent space is forced to produce increasingly valid structures and that the structure discriminator becomes fine-tuned to reject the increasingly smaller space of invalid structures that the VAE may produce, which therefore iteratively improves the percent of valid structures that the VAE produces and increase the discrimination power of the molecular structure discriminator.

* * * * *